United States Patent
Magaña Castro et al.

(10) Patent No.: US 11,576,905 B2
(45) Date of Patent: Feb. 14, 2023

(54) TOPICAL SEMISOLID COMPOSITION CONTAINING AN ANTIMICROBIAL AGENT AND PIRFENIDONE FOR THE TREATMENT OF CHRONIC SKIN DAMAGE

(71) Applicant: Excalibur Pharmaceuticals, Inc., New York, NY (US)

(72) Inventors: José Agustín Rogelio Magaña Castro, Mexico City (MX); Juan Socorro Armendáriz Borunda, Mexico City (MX)

(73) Assignee: Excalibur Pharmaceuticals, Inc., New York, NY (US)

( * ) Notice: Subject to any disclaimer, the term of this patent is extended or adjusted under 35 U.S.C. 154(b) by 6 days.

(21) Appl. No.: 16/638,621

(22) PCT Filed: Aug. 10, 2018

(86) PCT No.: PCT/MX2018/000071
§ 371 (c)(1),
(2) Date: Feb. 12, 2020

(87) PCT Pub. No.: WO2019/035705
PCT Pub. Date: Feb. 21, 2019

(65) Prior Publication Data
US 2020/0253944 A1    Aug. 13, 2020

(30) Foreign Application Priority Data
Aug. 15, 2017  (MX) .................... MX/a/2017/010486

(51) Int. Cl.
*A61K 31/4418*    (2006.01)
*A61P 17/02*      (2006.01)
(Continued)

(52) U.S. Cl.
CPC ........ *A61K 31/4418* (2013.01); *A61K 31/351* (2013.01); *A61P 17/02* (2018.01); *A61K 9/0014* (2013.01); *A61K 9/06* (2013.01)

(58) Field of Classification Search
CPC .............. A61K 31/4418; A61K 31/351; A61K 9/0014; A61K 45/06; A61K 47/10;
(Continued)

(56) References Cited

U.S. PATENT DOCUMENTS 4,105,782 A    8/1978 Yu et al.
4,376,118 A    3/1983 Daher et al.
(Continued)

FOREIGN PATENT DOCUMENTS

CN        1701793 A      11/2005
CN       101972225        2/2011
(Continued)

OTHER PUBLICATIONS

Alfonso, Remington's Pharmaceutical Sciences, 18th ed., 1990, p. 1288-1289, 1291-1292 (Year: 1990).*
(Continued)

*Primary Examiner* — Taylor V Oh
(74) *Attorney, Agent, or Firm* — Wolf, Greenfield & Sacks, P.C.

(57) ABSTRACT

The invention provides topical pharmaceutical gel compositions for the treatment of chronic skin damage, specifically for damage caused by neuropathic ulcers and preferably for the treatment of diabetic foot, and in the treatment of vascular ulcers wherein said compositions comprise a combination of Modified Diallyl Disulfide Oxide (M-DDO) (as an antiseptic/antibiotic agent) and 5-methyl-1-phenyl-2 (1H)-pyridone.
Furthermore, the invention describes methods of treatment, applications and/or pharmaceutical uses in the preparation of
(Continued)

medicaments for eliminating, reducing or preventing chronic skin lesions and the damages caused by neuropathic ulcers and particularly in the treatment of diabetic foot and in the treatment of vascular ulcers.

20 Claims, 9 Drawing Sheets

(51) Int. Cl.
  *A61K 31/351* (2006.01)
  *A61K 9/00* (2006.01)
  *A61K 9/06* (2006.01)
(58) Field of Classification Search
  CPC ............... A61K 47/32; A61K 36/8962; A61K 2300/00; A61K 9/06; A61P 17/02
  USPC ....................................................... 514/345
  See application file for complete search history.

(56) References Cited

U.S. PATENT DOCUMENTS

| | | | |
|---|---|---|---|
| 5,009,895 A | 4/1991 | Lui | |
| 5,310,562 A | 5/1994 | Margolin | |
| 5,811,130 A | 9/1998 | Boettner et al. | |
| 5,958,420 A | 9/1999 | Jenson | |
| 6,365,131 B1 | 4/2002 | Doshi et al. | |
| 7,109,246 B1 | 9/2006 | Hawtin | |
| 8,492,412 B2 | 7/2013 | Castro et al. | |
| 8,603,965 B2 | 12/2013 | Zhou et al. | |
| 9,408,836 B2 | 8/2016 | Borunda et al. | |
| 9,949,959 B2 | 4/2018 | Borunda et al. | |
| 9,962,374 B2 | 5/2018 | Borunda et al. | |
| 10,376,500 B2 | 8/2019 | Castro et al. | |
| 10,383,862 B2 | 8/2019 | Borunda et al. | |
| 10,792,258 B2 | 10/2020 | Magana Castro et al. | |
| 11,013,727 B2 | 5/2021 | Armendariz Borunda et al. | |
| 11,040,030 B2 | 6/2021 | Armendariz Borunda et al. | |
| 11,052,074 B2 | 7/2021 | Armendariz Borunda et al. | |
| 11,083,719 B2 | 8/2021 | Magana Castro et al. | |
| 2004/0029946 A1 | 2/2004 | Arora et al. | |
| 2004/0235946 A1 | 11/2004 | Ott | |
| 2005/0059626 A1 | 3/2005 | Van Nest et al. | |
| 2006/0039931 A1* | 2/2006 | Scheiwe | A61P 17/02 424/400 |
| 2006/0051339 A1 | 3/2006 | Sivak | |
| 2006/0115503 A1 | 6/2006 | Goyal | |
| 2007/0117841 A1 | 5/2007 | Ozes et al. | |
| 2007/0128258 A1 | 6/2007 | Faure et al. | |
| 2008/0319026 A1 | 12/2008 | Gant et al. | |
| 2009/0137354 A1 | 5/2009 | Chaudhuri | |
| 2010/0256031 A1 | 10/2010 | Wu et al. | |
| 2011/0224265 A1 | 9/2011 | Castro et al. | |
| 2013/0225639 A1 | 8/2013 | Robinson et al. | |
| 2013/0245073 A1 | 9/2013 | Castro et al. | |
| 2014/0296300 A1 | 10/2014 | Borunda et al. | |
| 2015/0148382 A1* | 5/2015 | Armendariz Borunda | A61P 17/00 514/345 |
| 2015/0231098 A1 | 8/2015 | Castro et al. | |
| 2016/0228424 A1 | 8/2016 | Borunda et al. | |
| 2016/0287567 A1 | 10/2016 | Borunda et al. | |
| 2017/0216268 A1 | 8/2017 | Castro et al. | |
| 2018/0092893 A1 | 4/2018 | Borunda et al. | |
| 2018/0214434 A1 | 8/2018 | Borunda et al. | |
| 2018/0353448 A1 | 12/2018 | Castro et al. | |
| 2019/0030012 A1 | 1/2019 | Surber | |
| 2019/0262325 A1 | 8/2019 | Borunda et al. | |
| 2019/0290606 A1 | 9/2019 | Castro et al. | |
| 2019/0358213 A1 | 11/2019 | Borunda et al. | |
| 2020/0016138 A1 | 1/2020 | Castro et al. | |
| 2020/0038386 A1 | 2/2020 | Armendariz Borunda et al. | |
| 2020/0061040 A1 | 2/2020 | Borunda et al. | |
| 2020/0253944 A1 | 8/2020 | Magana Castro et al. | |
| 2021/0093593 A1 | 4/2021 | Magana Castro et al. | |
| 2021/0346360 A1 | 11/2021 | Armendariz Borunda et al. | |
| 2021/0386724 A1 | 12/2021 | Armendariz Borunda et al. | |
| 2021/0401989 A1 | 12/2021 | Armendariz Borunda et al. | |
| 2022/0016096 A1 | 1/2022 | Magana Castro et al. | |

FOREIGN PATENT DOCUMENTS

| | | |
|---|---|---|
| CN | 101972236 A | 2/2011 |
| CN | 102670632 A | 9/2012 |
| CN | 103550242 A | 2/2014 |
| EP | 1 356 816 A1 | 10/2003 |
| EP | 2177220 A1 | 4/2010 |
| EP | 2832354 A1 | 2/2015 |
| EP | 2 907 506 A1 | 8/2015 |
| JP | 2011-506446 A | 3/2011 |
| JP | 2014-522861 | 9/2014 |
| JP | 2015-513359 A | 5/2015 |
| JP | 2015-526528 A | 9/2015 |
| JP | 2016-517444 A | 6/2016 |
| MX | 2013008151 A | 10/2013 |
| WO | 99/047140 A1 | 9/1999 |
| WO | 99/47140 A1 | 9/1999 |
| WO | 0016775 A1 | 3/2000 |
| WO | 2004/073713 A1 | 9/2004 |
| WO | 2005/000227 A2 | 1/2005 |
| WO | 2006/122154 A2 | 11/2006 |
| WO | 2007/038315 A2 | 4/2007 |
| WO | 2008107873 A1 | 9/2008 |
| WO | 2009/022899 A1 | 2/2009 |
| WO | WO 2010/054294 | 5/2010 |
| WO | 2013/012307 A1 | 1/2013 |
| WO | 2013/147577 A1 | 10/2013 |
| WO | WO 2014/036487 | 3/2014 |
| WO | 2014/055548 A1 | 4/2014 |
| WO | WO 2017/104725 A1 | 6/2017 |
| WO | WO 2018/088886 | 5/2018 |
| WO | 2019/035705 A2 | 2/2019 |

OTHER PUBLICATIONS

U.S. Appl. No. 16/348,189, filed May 8, 2019, Juan Socorro Armendáriz Borunda.
U.S. Appl. No. 16/371,670, filed Apr. 1, 2019, José Agustín Rogelio Magaña Castro.
U.S. Appl. No. 16/008,210, filed Jun. 14, 2018, José Agustín Rogelio Magaña Castro.
U.S. Appl. No. 14/421,616, filed Feb. 13, 2015, José Agustín Rogelio Magaña Castro.
U.S. Appl. No. 16/450,150, filed Jun. 24, 2019, José Agustín Rogelio Magaña Castro.
U.S. Appl. No. 15/435,494, filed Feb. 17, 2017, José Agustín Rogelio Magaña Castro.
U.S. Appl. No. 13/893,626, filed May 14, 2013, José Agustín Rogelio Magaña Castro.
U.S. Appl. No. 12/673,304, filed Apr. 28, 2010, José Agustín Rogelio Magaña Castro.
U.S. Appl. No. 16/460,407, filed Jul. 2, 2019, Juan Armendáriz Borunda.
U.S. Appl. No. 15/831,650, filed Dec. 5, 2017, Juan Armendáriz Borunda.
U.S. Appl. No. 15/177,760 filed Jun. 9, 2016, Juan Armendáriz Borunda.
U.S. Appl. No. 14/233, 600, filed May 20, 2014, Juan Armendáriz Borunda.
U.S. Appl. No. 16/534,980, filed Aug. 7, 2019, Juan Socorro Armendáriz Borunda.
U.S. Appl. No. 15/920,822, filed Mar. 14, 2018, Juan Socorro Armendáriz Borunda.
U.S. Appl. No. 15/098,970, filed Apr. 14, 2016, Juan Armendáriz Borunda.
U.S. Appl. No. 14/388,447, filed Feb. 5, 2015, Juan Armendáriz Borunda.
Office Action, U.S. Appl. No. 16/371,670, dated Aug. 7, 2019.
Office Action, U.S. Appl. No. 16/008,210, dated Oct. 1, 2018.

(56) References Cited

OTHER PUBLICATIONS

Office Action, U.S. Appl. No. 14/421,616, dated Dec. 14, 2017.
Office Action, U.S. Appl. No. 14/421,616, dated Mar. 6, 2017.
Office Action, U.S. Appl. No. 14/421,616, dated May 19, 2016.
Office Action, U.S. Appl. No. 14/421,616, dated Nov. 9, 2015.
Office Action, U.S. Appl. No. 15/435,494, dated Apr. 3, 2019.
Office Action, U.S. Appl. No. 15/435,494, dated Sep. 20, 2018.
Office Action, U.S. Appl. No. 15/435,494, dated Jan. 26, 2018.
Office Action, U.S. Appl. No. 15/435,494, dated Sep. 8, 2017.
Office Action, U.S. Appl. No. 13/893,626, dated Aug. 22, 2016.
Office Action, U.S. Appl. No. 13/893,626, dated Dec. 17, 2015.
Office Action, U.S. Appl. No. 13/893,626, dated Apr. 14, 2015.
Office Action, U.S. Appl. No. 12/673,304, dated Mar. 8, 2013.
Office Action, U.S. Appl. No. 12/673,304, dated Jun. 20, 2012.
Office Action, U.S. Appl. No. 12/673,304, dated Mar. 14, 2012.
Office Action, U.S. Appl. No. 15/831,50, dated Jun. 26, 2019.
Office Action, U.S. Appl. No. 15/831,650, dated Mar. 19, 2019.
Office Action, U.S. Appl. No. 15/831,650, dated Oct. 2, 2018.
Office Action, U.S. Appl. No. 15/831,650, dated Jun. 13, 2018.
Office Action, U.S. Appl. No. 15/177,760, dated Jan. 24, 2018.
Office Action, U.S. Appl. No. 15/177,760, dated Apr. 17, 2017.
Office Action, U.S. Appl. No. 15/177,760, dated Dec. 15, 2016.
Office Action, U.S. Appl. No. 14/233,600, dated Jun. 14, 2016.
Office Action, U.S. Appl. No. 14/233,600, dated Nov. 23, 2015.
Office Action, U.S. Appl. No. 14/233,600, dated Jul. 8, 2015.
Office Action, U.S. Appl. No. 15/920,822, dated Feb. 7, 2019.
Office Action, U.S. Appl. No. 15/920,822, dated Nov. 15, 2018.
Office Action, U.S. Appl. No. 15/098,970, dated Dec. 15, 2017.
Office Action, U.S. Appl. No. 15/098,970, dated Mar. 23, 2017.
Office Action, U.S. Appl. No. 15/098,970, dated Jan. 11, 2017.
Office Action, U.S. Appl. No. 14/388,447, dated Oct. 15, 2015.
Office Action, U.S. Appl. No. 16/450,150, dated Nov. 1, 2019.
Office Action, U.S. Appl. No. 16/460,407, dated Apr. 6, 2020.
Office Action, U.S. Appl. No. 16/460,407, dated Nov. 26, 2019.
Office Action, U.S. Appl. No. 16/534,980, dated Apr. 15, 2020.
Allicinnow, "allicin," retrieved online at: http://www.allicinnow.com/allicin/acne-treatment/, 2 pages (2010).
Armendariz-Borunda, Juan et al., "A Controlled Clinical Trial With Pirfenidone in the Treatment of Pathological Skin Scarring Caused by Burns in Pediatric Patients," Annals of Plastic Surgery, vol. 68(1):22-28 (2012).
Database WPI Section Ch, Week 200629 Thomson Scientific, London, GB; Class B03, AN 2006-273778, WU J "Use of pirfenidone for treating hepatic injury and necrosis and acute lung injury," Shanghai Genomics, p. 7 (2005).
Database WPI Section Ch, Week 201139 Thomson Scientific, London, GB; Class A96, AN 2011-D92901, Li X "Sustained-release tablet comprises pirfenidone, substance capable of releasing active ingredient, and additive", Med Pharm Sci&Technology Co , 1 page (2011).
Database WPI Section Ch, Week 201427 Thomson Scientific, London, GB; Class A96, AN 2014-F77081, Deng C et al., "Pharmaceutical composition used for treating hepatic fibrosis, liver fibrosis, liver cirrhosis, and liver cancer comprises pirfenidone, inosine, and auxiliary materials", Sichuan Guokang Pharm Co Ltd, 1 page (2014).
Gad, C.G., "Pharmaceutical Manufacturing Handbook: production and processes," John Wiley & Sons, ISBN: 978-0-470-25958-0, 1386 pages (Mar. 2008).
Garcia et al., "Pirfenidone effectively reverses experimental liver fibrosis", Journal of Hepatology, vol. 37, No. 6, pp. 797-805 (2002).
International Preliminary Report on Patentability, PCT/MX2018/000071, dated Jul. 19, 2019, 7 pages.
International Search Report and Written Opinion, PCT/MX2018/000071, dated Mar. 28, 2019, 12 pages.
Josling, Peter, "Peter Josling's PowerPoint on AllicinCenter Products and Their Uses," retrieved from the internet at: http://allicincenter.com/reference.php?id=products, 15 pages (2013).
Macias-Barragan J. et al., "Methyl-1-Phenyl-2- (1H)—Pyridone Treatment Improves Markers of Hepatic Function and Fibrosis in Steatosis Included By High Fat/Carbohydrate Diet," Journal of Hepatology, Abstract of the International Liver Congress™ 2014—49th Annual Meeting of the European Association for the Study of the Liver, Abstract P428, vol. 60(1)Suppl.1: S210 (2014).
Macias-Barragan, O. et al., "Pirfenidone LP activates PPARalpha and LXRalpha and results in decreased expression of proinflammatory cytokines and improvement of NASH features induced by high fat/carbohydrate diet," Hepatology—Special Issue: The 67th Annual Meeting of the American Association for the Study of Liver Diseases: The Liver Meeting 2016, Abstract No. 1541: vol. 64(SI): 767A-768A: 2 pages (2016).
Nakanishi, H. et al., "Pirfenidone inhibits the induction of iNOS stimulated by interleukin-lbeta at a step of NF-kappaB DNA binding in hepatocytes," Journal of Hepatology, vol. 41(5):730-736 (2004).
Ozes O., et al., "Preclinical activity of pirfenidone (5-methyl-lphenyl -2 (IH) -pyridone) in cell-based models of nonalcoholic steatohepatitis," Hepatology, Abstract 697, vol. 34(4): 495A (2003).
Tiwari, S., et al., "Applications of Complementary Polymers in HPMC Hydrophilic Extended Release Matrices," Drug Delivery Technology, Formulating Hydrophilic Matrix Systems, vol. 9(7), 7 pages (2009).
Veras-Castillo, ER et al., "Controlled clinical trial with pirfenidone in the treatment of breast capsular contracture: association of TGF-beta polymorphisms," Annals of Plastic Surgery, vol. 70(1), pp. 16-22 (2014).
WebMD. "Understand Acne Treatment." Retrieved Feb. 4, 2019. Retrieved from internet <URL: https://www.webmd.com/skin-problems-and-treatments/acne/understanding-acne-treatnnent#5>. (Year: 2019); 5 pages.
International Preliminary Report on Patentability dated Aug. 7, 2013 for Application No. PCT/MX2012/000067.
International Search Report and Written Opinion dated Nov. 22, 2012 for Application No. PCT/MX2012/000067.
International Preliminary Report on Patentability dated Dec. 1, 2009 for Application No. PCT/MX2008/000107.
International Search Report dated Dec. 9, 2008 for Application No. PCT/MX2008/000107.
International Preliminary Report on Patentability dated Jan. 28, 2018 for Application No. PCT/MX2017/000129.
International Search Report and Written Opinion dated Apr. 9, 2018 for Application No. PCT/MX2017/000129.
International Search Report and Written Opinion dated Jun. 5, 2013 for Application No. PCT/MX2013/000027.
International Preliminary Report on Patentability dated Dec. 19, 2014 for Application No. PCT/MX2013/000099.
International Search Report and Written Opinion dated Aug. 8, 2014 for Application No. PCT/MX2013/000099.
Ojeda-Duran et al., Evaluation of Safety of a Newly Formulated Pirfenidone in Chronic Kidney Disease: A Non-Randomized Pilot Study in Mexican Patients. J Renal Hepatic Disorders. 2020;4(1):22-30.
PCT/MX2012/000067, Aug. 7, 2013, International Preliminary Report on Patentability.
PCT/MX2012/000067, Nov. 22, 2012, International Search Report and Written Opinion.
PCT/MX2008/000107, Dec. 1, 2009, International Preliminary Report on Patentability.
PCT/MX2008/000107, Dec. 9, 2008, International Search Report and Written Opinion.
PCT/MX2017/000129, Jan. 28, 2018, International Preliminary Report on Patentability.
PCT/MX2017/000129, Apr. 9, 2018, International Search Report and Written Opinion.
PCT/MX2013/000027, Jun. 5, 2013, International Search Report and Written Opinion.
PCT/MX2013/000099, Dec. 19, 2014, International Preliminary Report on Patentability.
PCT/MX2013/000099, Aug. 8, 2014, International Search Report and Written Opinion.
International Preliminary Report on Patentability dated Dec. 9, 2014 for Application No. PCT/MX2013/000027.

(56) References Cited

OTHER PUBLICATIONS

International Search Report and Written Opinion, for Application No. PCT/US2021/027335, dated Jul. 12, 2021.
International Search Report and Written Opinion, for Application No. PCT/MX2019/000093, dated Aug. 4, 2020.
International Preliminary Report on Patentability, for Application No. PCT/MX2019/000093, dated Jan. 12, 2021.
ClinicalTrials.gov archive NCT02632877. Efficacy of Pirfenidone Plus MODD in Diabetic Foot Ulcers. Last updated: Dec. 17, 2015. Retreived: May 17, 2022. 8 pages. <URL:https://clinicaltrials.gov/ct2/show/NCT02632877?term=NCT02632877&draw=2&rank=1>.
Gancedo et al., Pirfenidone prevents capsular contracture after mammary implantation. Aesthetic Plast Surg. Jan. 2008;32(1):32-40. doi: 10.1007/s00266-007-9051-4. PMID: 17968613.
Janka-Zires et al., Topical Administration of Pirfenidone Increases Healing of Chronic Diabetic Foot Ulcers: A Randomized Crossover Study. J Diabetes Res. 2016;2016:7340641. doi: 10.1155/2016/7340641, Epub Jul. 10, 2016.
Kharkevich, Pharmacology Total Formulation. 10th Edition. 2010. pp. 76-77.
Orozco et al., Economic Evaluation Of Topical Administration of Gel With Pirfenidone (Kitoscell Q®) as an Adjuvant in The Treatment of Patients With Diabetic Foot Ulcers. PMD63, Value in Health, May 2017; 20(5): A246.
Wang et al., Remdesivir and chloroquine effectively inhibit the recently emerged novel coronavirus (2019-nCoV) in vitro. Cell Res. Mar. 2020;30(3):269-271. doi: 10.1038/s41422-020-0282-0, Epub Feb. 4, 2020, PMID: 32020029; PMCID: PMC7054408.
Bednarek et al., Skin Antiseptics. In:StatPearls. Jan. 2022. Retrieved from https://www.ncbi.nlm.nih.gov/books/NBK507853 Jun. 9, 2022.

* cited by examiner

TOPICAL SEMISOLID COMPOSITION CONTAINING AN ANTIMICROBIAL AGENT AND PIRFENIDONE FOR THE TREATMENT OF CHRONIC SKIN DAMAGE

RELATED APPLICATIONS

This application is a national stage filing under 35 U.S.C. § 371 of international PCT application, PCT/MX2018/000071, filed Aug. 10, 2018, which claims priority under 35 U.S.C. § 119(a) to Mexican Patent Application, MX/A/2017/010486, filed Aug. 15, 2017, each of which is incorporated herein by reference.

FIELD OF THE INVENTION

The present invention relates to topical semisolid (water-soluble) pharmaceutical compositions in gel form comprising a combination of 5-methyl-1-phenyl-2(1H)pyridone and an antimicrobial agent, being this agent: Modified Diallyl Disulphide Oxide (M-DDO), said compositions are useful in the treatment of chronic skin damage, specifically of skin ulcers that can be of diabetic origin, or vascular ulcers. Also, the invention also relates to methods for the treatment of said chronic skin damage and to a process for the manufacture of the topical pharmaceutical composition in gel.

BACKGROUND OF THE INVENTION

The word ulcer comes from the Latin ulcer plural of ulcus, sore. It is defined as a continuity solution with loss of substance from any epithelial surface of the organism, with little or no tendency to spontaneous healing. Is also accepted the definition of more specific pathological processes, such as loss of skin or mucous substance, consequence of a pathological process, which in depth affect at least subepithelial connective tissue. Ulcers due to trauma are called wounds.

The ulcers can reach the superficial or deep dermis, the hypodermis or they can reach the fascia, and even the underlying bone. Due to its evolution, ulcers can be classified generically as acute and chronic.

Ulceration is any loss of the substance of the skin, if it is superficial, it is called erosion or exulceration, such as a blister that breaks; if the germinative layer is not injured, there will be no scar.

The ulceration can cover all the layers of the skin and reach the subcutaneous cellular tissue and even deep planes. When they are linear, they are known as fissures or cracks.

Chronic ulceration is the solution of continuity with loss of substance from any epithelial surface of the organism, with little or no tendency to spontaneous and long-lasting scarring (>6 weeks) or with frequent recurrence.

The process of tissue regeneration is given by a balance between degradation and synthesis of new tissue, through three phases: inflammation, proliferation and remodeling. When there is an imbalance between the production and degradation of tissue, it results in the chronic presence of an epithelial lesion in the form of an ulcer, that is, a solution of continuity of the epithelial surface, which tends to a slight healing.

In ulcers, chronic inflammation due to infection, necrotic tissue or foreign bodies, favors the release of inflammatory cytokines such as tumor necrosis factor alpha (TNFα), interleukin-1 (IL-1), interleukin-6 (IL-6), interleukin-8 (IL-8) as well as metalloproteases whose function is to degrade extracellular matrix proteins. Therefore, upon raising the levels of metalloproteases, the destruction of the extracellular matrix is favored.

A key cytokine in this pathophysiological process is the transforming growth factor beta-1 (TGF-β1). TGF-β1 stimulates the process of fibrogenesis and modulates the activity of some growth factors such as vascular endothelial growth factor (VEGF), platelet-derived growth factor (PDGF) and keratinocyte growth factor (KGF), among others.

In chronic injuries, the balance of the process is broken regardless of the type of ulcer problem the patient attends. It can be said, that the alterations in the process of tissue regeneration are due to alterations in the balance between the production of new tissue and the degradation effects that cause a lesion to become chronic.

Among the chronic ulcers, which are increasingly affecting the population, are diabetic foot ulcers, pressure or decubitus ulcers (bedsores), as well as vascular, arterial and venous ulcers.

Since the alterations in the process show deficiencies in the expression of growth factors, it has been sought to control these alterations, being studied among others, the Platelet Derived Growth Factor (PDGF) and the Granulocyte Colony Stimulating Factor (GCSF).

Unfortunately, GF despite its promising results, have the disadvantage that still need to be obtained by complex biotechnological processes and their production, more than difficult, it is expensive; what affects the treatment of the patient.

Diabetic Foot

Diabetic foot is a clinical entity that refers to the resulting syndrome from the interaction of predisposing factors (such as angiopathy, neuropathy and infection), upon extrinsic and intrinsic triggers (such as trauma, local hygiene and bone deformities), due to chronic hyperglycemia present in the diabetic patient.

Such syndrome is considered one of the complications of diabetes mellitus, being the most common cause of non-traumatic amputation in people over 50 years of age. 85% of amputations are preceded by an ulcer in the foot, which decreases the quality of life of the patient since only one third of these patients walk again using prosthesis. Added to this, approximately 30% of these patients die in the first year and it is estimated that, after 5 years, 50% suffer amputation of the other limb.

Vascular Ulcers

Are classified as:

Arterial ulcers,

Venous ulcers.

Arterial Ulcers

Represent the second cause of skin ulcers on the legs. Are those ulcers produced by arterial insufficiency, with loss of arterial blood supply by either, chronic arterial vasoconstriction, obstruction or malformation.

Obstruction, vasoconstriction and arterial malformation They occur in scleroderma, extramural processes, progeria, arteriosclerosis, vasculitis, vaso-spastic disorders, thrombosis, embolism, Raynaud's phenomenon, coagulation disorders and tissue scars.

Appearance and Location

Arterial ulcers are of variable size, from a few millimeters to several centimeters, sometimes occurring on the entire surface of the leg, may be single or multiple ulcer, oval, round or irregular, unilateral or bilateral, with borders well defined (discretely elevated) and atrophic background, gray or black base, with little granulation tissue. They are usually located in bony prominences and metatarsal heads, mainly in the middle perimalleolar area, frequently in the inner region of the lower third of the leg.

Venous Ulcers

Represent the most frequent cause of cutaneous ulcers in the legs. The majority of chronic ulcers in the lower pelvic limbs are secondary to chronic venous stasis due to postphlebitic syndrome or arteriovenous shunts.

They are also defined as ulcers produced by chronic venous insufficiency, given by valvular incompetence.

Appearance and Location

Venous ulcers present with ill-defined borders (irregular and elevated) and granulomatous fundus. They are usually located on the inner side region of pelvic limbs.

Bedsores

Produced by pressure, friction or continuous friction of the tissues between two planes, that is, the bony prominence of the patient and an external surface, for a prolonged period.

The developed invention comprises the combination of an antimicrobial agent and 5-methyl-1-phenyl-2(H)pyridone (Pirfenidone), which application in the treatment of chronic ulcers has given results that have exceeded therapeutic expectations.

Antibiotic is defined as "those chemical substances produced by various species of microorganisms (bacteria, ascomycetes and fungi) or chemically synthesized, which have the ability to inhibit the growth of microorganisms and cause their destruction". Several formulations have been designed for systemic and topical use, which indication is based on the therapeutic needs determined by the nature of the patient's infectious condition and the medical criteria. When we speak of antimicrobial agents, a large arsenal of substances is included, ranging from antibacterial (antibiotics), antituberculous agents, antifungals, antiseptics to antiviral agents.

Topical antibiotic agents have a fundamental role in dermatology and represent an option against systemic agents in highly localized skin infections and without systemic compromise, for both outpatients and inpatients.

Topical antibiotics have a more selective toxicity that allows them to inhibit the development of bacterial cells or destroy them respecting the host cells. Topical antibiotics can create microbial resistances and cause sensitization by cross-reactions. It is considered as an ideal topical antibiotic when it has the following characteristics:

1. A broad spectrum of activity for skin pathogens.
2. A persistent antibacterial effect.
3. Low capacity to induce resistance.
4. Absence of cross-resistance with antibiotics for systemic use.
5. Good tolerability, low incidence of allergy.
6. Minimum or absence of toxicity and incidence of allergy.
7. Penetration in skin and scabs.
8. Low cost.

Antimicrobial Characterization of M-DDO

Diallyl Disulfide Oxide (ODD) also known as allicin, is the product of the catalysis of the aliin, found in garlic (*Allium sativum*), by the intervention of the enzyme allinase. It is a sulfur compound that has various pharmacological activities of interest. By virtue of being a very unstable compound, ODD loses its properties quickly. It has been shown that ODD has in vitro activity against *Candida albicans*, some species of *Trichomonas*, *Staphylococcus aureus*; *Escherichia coli*, *Salmonella typhi*, *S. paratyphi*, *Shigella dysenterica* and *Vibro cholerae*.

Through a process of semi-synthetic synthesis, it has been possible to stabilize the Diallyl Disulfide Oxide, adding a cofactor. The resulting compound is called Modified Disulfide Diallyl Oxide [M-DDO], which is much more stable than allicin and apparently retains its properties.

Modified Diallyl Disulphide Oxide [M-DDO], is the chemical compound called [1,2-diallyl-1-(5-methyl-tetrahydro-2H-pyran-2-yloxy)disulfuronium]+6- [(benzyl, methyl, octylammonium) (hydroxymethylamine)(methylamine)]-tetrahydro-2H-pyran-3-oxy]chloride; which structural formula is represented below:

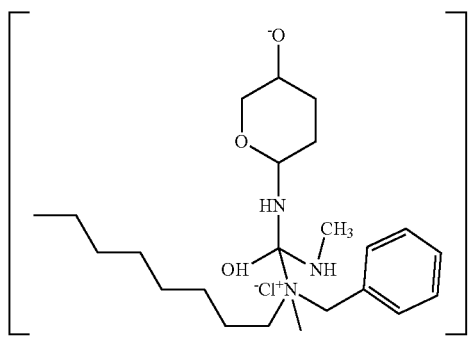

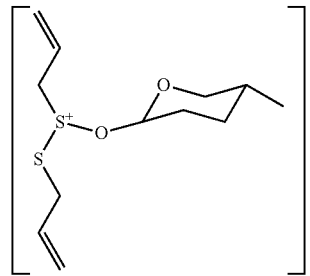

In several investigations published in refereed journals, the activity of allicin has been demonstrated; however, its poor stability has been a limitation in its possible therapeutic applications. Consequently, it is clear that the use of the stability properties of the M-DDO complex will allow its therapeutic application based on the antibacterial and antiseptic properties, among other known properties of allicin. This antimicrobial agent meets the aforementioned characteristics of an ideal antimicrobial because it has a broad spectrum of activity for skin pathogens, has a persistent antibacterial effect, has a low capacity to induce resistance due to its triple antimicrobial action mechanism, and does not present cross-resistance with antibiotics for systemic use. Has good tolerability, low incidence of allergy and minimal or no toxicity and incidence of allergy.

The M-DDO molecule is described in the patent application number MX 2012003874 A, which gives the present invention an additional novel feature, by using an innovative molecule for its pharmacological use.

Characterization of Pirfenidone

Complementarily, 5-methyl-1-phenyl-2(1H)-pyridone, which structural formula is shown below:

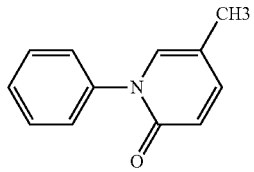

Is a drug that has been applied in the restoration of tissues with injuries that occur with fibrosis and for the prevention of fibrotic injuries. Such compound, called Pirfenidone, is itself a known compound and its pharmacological effects have been described in, for example, Japanese applications KOKAI Nos. 87677/1974 and 1284338/1976, as an antiinflammatory agent that includes antipyretics and analgesics effects. U.S. Pat. No. 3,839,346, published on Oct. 1, 1974, U.S. Pat. No. 3,974,281, published on Aug. 10, 1976, U.S. Pat. No. 4,042,699, published on Aug. 16, 1977, and U.S. Pat. No. 4,052,509, published on Oct. 4, 1977, describe methods for obtaining Pirfenidone, as well as its use as an anti-inflammatory agent, since it acts as:

1. A potent inhibitor of factors that act in the inflammatory phase of healing (TNF-alpha, IL-1, IL-6).
2. Powerful inhibitor of NFkB. This transcriptional factor is the most important in the regulation of the transcription of genes that code for pro-inflammatory cytokines TNF-α, IL-1 and IL-6.
3. Cytokines regulator that stimulate fibroblasts and keratinocytes to promote the production of collagen fibers and the formation of granulation tissue necessary to "fill" the wound, an example of this is TGF-β1, considered the main profibrogenic cytokine.
TGF-beta 1 (Transforming Growth Factor Beta 1).
4. Potent inducer of TGF-beta 3 production, that acts as re-epithelization agent.
5. Powerful enzyme modulator (at the genetic and protein level) called metalloproteases (collagenases) that are responsible for degrading fibrotic tissue.
6. Powerful MODULATOR of TIMPs (Tissue Inhibitors of Metalloproteases) which allows REGULATING the action of the enzymes described above and that help in the remodeling of the tissue.
7. A modulator of the action of other important cytokines involved in the regenerative process of tissues: VEGF, PDGF, FGF, KGF, etc. Because these are "coordinated" by TGF-beta 3, which has proven to be a pluripotential element that acts by regulating the action of these factors.
8. Regulator of the oxide-reduction state in the wound. It decreases the production of reactive oxygen species (ROS) that perpetuate the oxidation of the wound and the inflammatory state.
9. Promoter of the expression of genes that encode ANTIOXIDANTS enzymes such as catalase (CAT), catalytic and regulatory fractions of glutamyl cysteine synthetase (GCLC and GCLM) and Hemo-oxygenase 1 (HMO1).
10. These events described in the previous point results in the sequestration and elimination of reactive oxygen species (ROS) and in the increased production of reduced glutathione, one of the most potent antioxidant systems in the human body.

OBJECTS OF THE INVENTION

It is a first object of the present invention to provide topical pharmaceutical gel compositions for the treatment of chronic skin damage, specifically for damage caused by neuropathic ulcers and preferably for the treatment of diabetic foot. Vascular ulcers can also be treated with this invention. Wherein such compositions comprise a combination of an antimicrobial agent and 5-methyl-1-phenyl-2(1H)-pyridone (Pirfenidone).

A second object is to obtain gel compositions comprising a combination of Modified Diallyl Disulfide Oxide (M-DDO) and 5-methyl-1-phenyl-2(1H)-pyridone for topical application which are stable, biodegradable, nontoxic, having wide spectrum of action, not only against chronic skin damage, specifically for damage caused by neuropathic ulcers and preferably in the treatment of diabetic foot and in the treatment of vascular ulcers.

Other objects of the invention are to provide a method for the treatment of chronic skin damage and, in addition, a process for the manufacture of a topical gel pharmaceutical composition comprising a combination of an antimicrobial agent and 5-methyl-1-phenyl-2(1H)-pyridone.

The above objectives are representative, but should not be considered as limiting the present invention, where treatment methods, applications or pharmaceutical uses are also shown in the preparation of drugs to eliminate, reduce or prevent chronic skin lesions and the damages caused by neuropathic ulcers and particularly in the treatment of diabetic foot and in the treatment of vascular ulcers.

DESCRIPTION OF THE INVENTION

Figure 1:
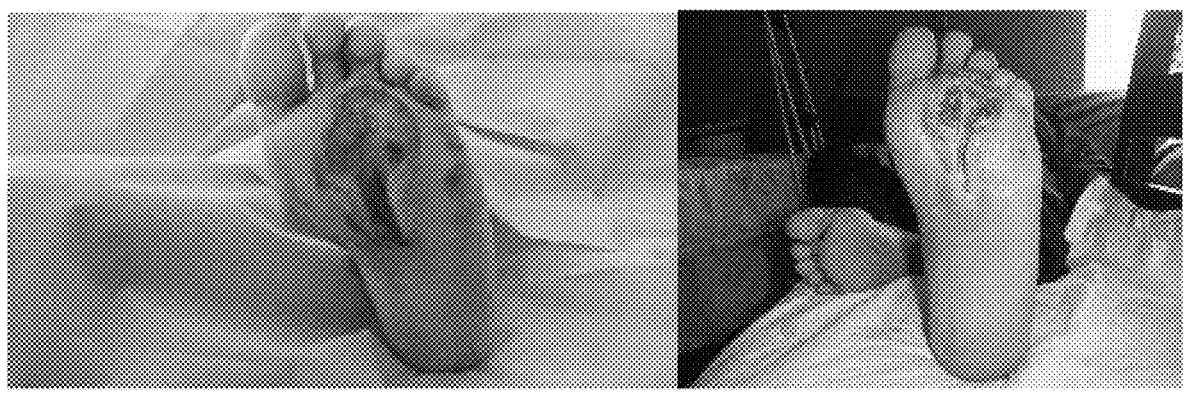
FIG. 1. 67 years old male treated with pirfenidone with an initial RUV of 48 cm and an RRUV of 91.7%
Figure 2:
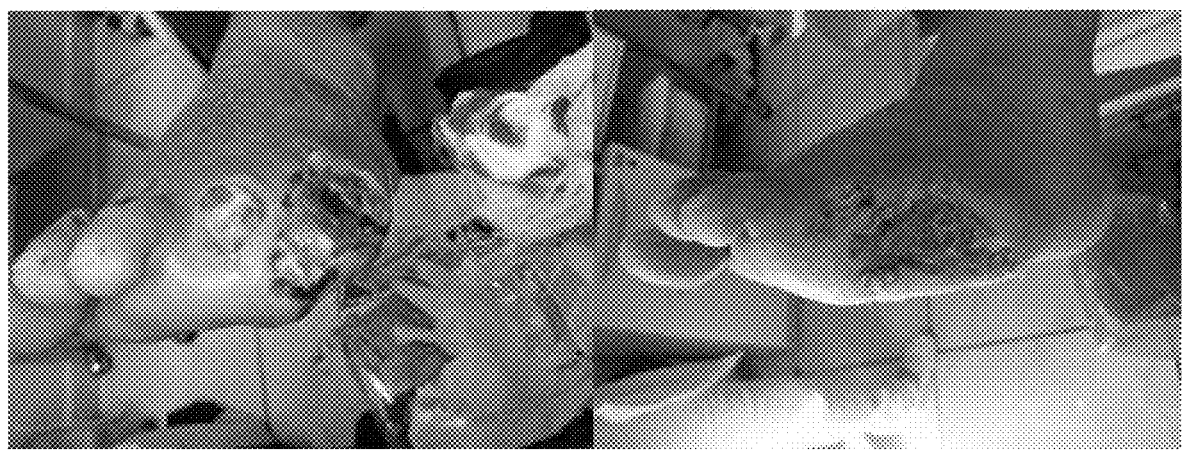
FIG. 2. 53 years old male treated with pirfenidone with an initial RUV of 18 cm and an RRUV of 88.3%
Figure 3:
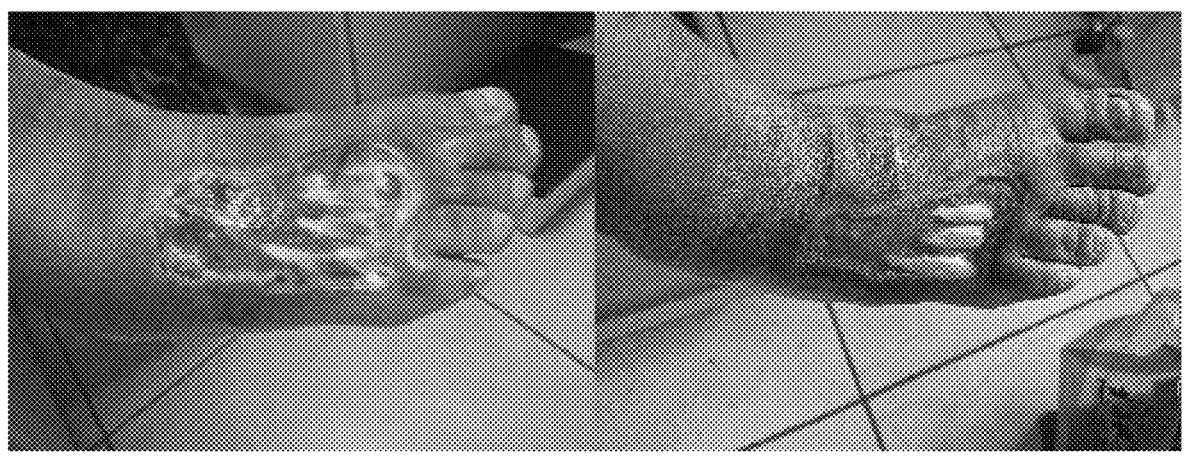
FIG. 3. 47 years old male treated with pirfenidone with an initial RUV of 11.8 cm and an RRUV of 71.2%
Figure 4:
FIG. 4. 49 years old male treated with pirfenidone with an initial RUV of 6.4 cm and an RRUV of 93.8%
Figure 5:
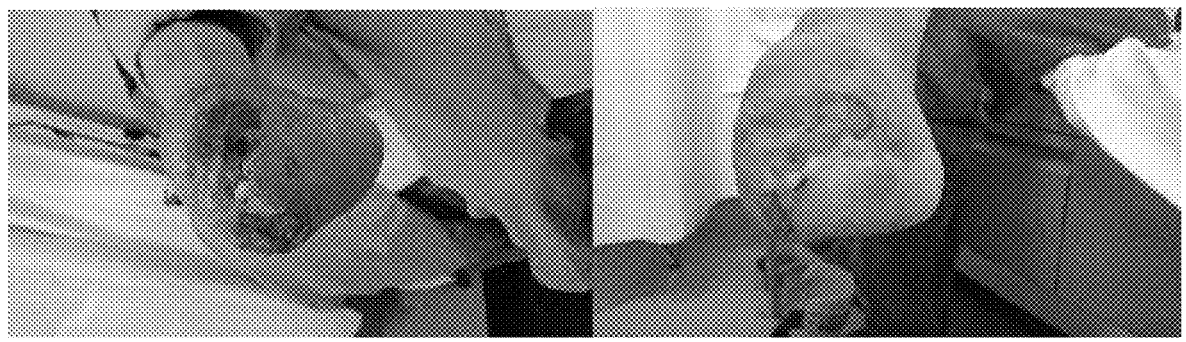
FIG. 5. 63 years old male treated with pirfenidone with an initial RUV of 16 cm and an RRUV of 80.9%
Figure 6:
FIG. 6. 67 years old female treated with ketanserin with an initial RUV of 2.5 cm and an RRUV of 38.8%
Figure 7:
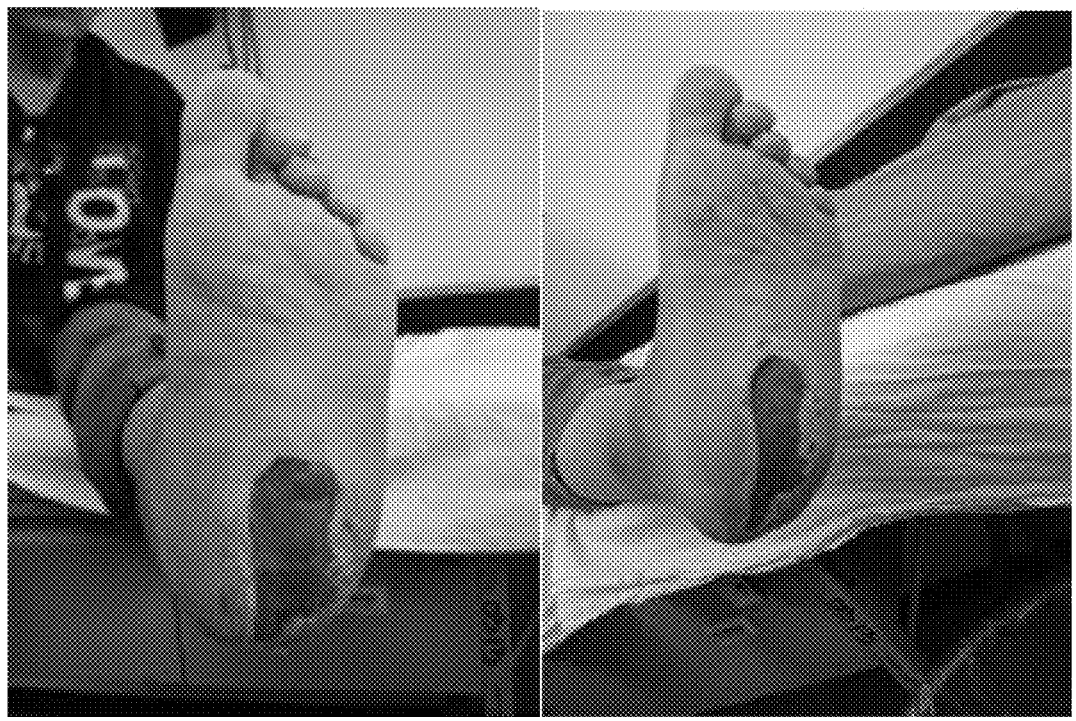
FIG. 7. 56 years old male treated with ketanserin with an initial RUV of 5.9 cm and an RRUV of 27% FIG. 8. 53 years old female treated with ketanserin with an initial RUV of 42 cm and an RRUV of 26.6%
Figure 8:
Figure 9:
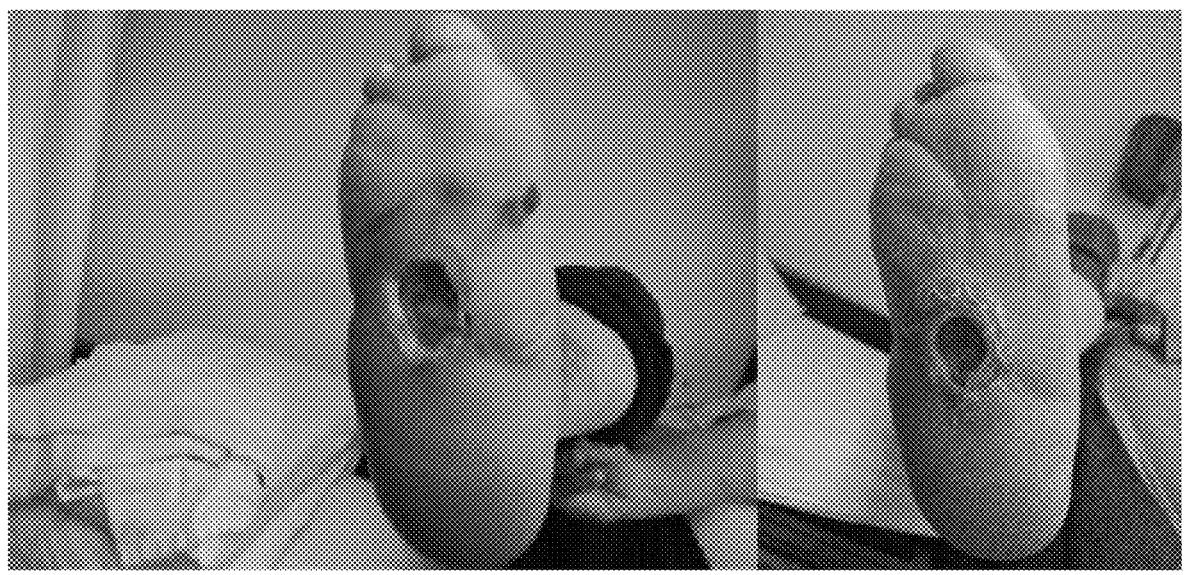
FIG. 9. 57 years old male treated with ketanserin with an initial RUV of 5 cm and an RRUV of 40%

The present invention relates to topical pharmaceutical compositions comprising a combination of 5-methyl-1-phenyl-2(1H)-pyridone (Pirfenidone) and some topical antibiotic agent, which comprise 0.01 to 5% w/w of the antimicrobial agent, from 5% to 10% w/w of the composition of 5-methyl-1-phenyl-2(1H)-pyridone, and from 85 to 95% w/w of the composition of one or more suitable excipients for the preparation of the gel.

Specifically, the invention relates to topical pharmaceutical compositions comprising a combination of Modified Diallyl Disulfide Oxide (M-DDO) and 5-methyl-1-phenyl-2(1H)-pyridone (Pirfenidone) topically applied, which comprise 0.01 to 0.1% weight/weight of the composition of M-DDO, 5% to 10% weight/weight of the composition of 5-methyl-1-phenyl-2(1H)-pyridone, and 89% to 95% weight/weight of the composition of one or more suitable excipients for the preparation of the gel.

Formulation of Topical Gels

The topical application of the combination of the aforementioned molecules is clearly reinforced by the formulation of the pharmaceutical compositions in gel form.

They are called gels (from the Latin gelu—cold, or gelatus—frozen, immobile) to transparent colloids; semisolids, which can be suspensions of small inorganic particles, or large organic molecules interpenetrated by a liquid that do not usually have fatty oils, intended to be applied on the mucous membranes, have no penetration power, that is why it is used to exert topical action (from surface). The common characteristic of them is the presence of a type of continuous structure that gives them the properties of semisolids.

The fact that an active substance is adsorbed, penetrates, permeates the skin or is absorbed, depends on its physical and chemical properties, such as its solubility in water, its lipid-water partition coefficient, its dissociation constant, its chemical structure and its molecular weight. In addition, it depends on the properties of the active principle once it is incorporated in a pharmaceutical form, for example, the pH, the nature of the vehicle, etc., as well as the type of barrier that will cross, which may present morphological and functional variations and others such as the presence of electric charges.

In the absorption site, the active ingredient must cross a lipid rod, which can be a complex barrier such as skin or the intestinal epithelium. This passage can be carried out according to several mechanisms:

| Passive diffusion | Facilitated diffusion |
| --- | --- |
| Conective absorption | Absorption by ion-couple |
| Active transport | Pinocytosis |

In the design of a gel, it is essential to select a formulation that presents organoleptic and rheological characteristics suitable for its topical administration, with appropriate extensibility and texture. It is also important to make sure that the preparation is aesthetically acceptable to the patient and easy to use.

Several factors must be keep in mind:
Choice of the active ingredients necessary to obtain the desired therapeutic action.
Choice of the pharmaceutical form and suitable excipients.
Evaluation of the compatibility of the active principles with the possible excipients.
Consideration of the dermatological effects of the vehicle.
Gels can by classified into:
Organic or inorganic according to their nature.
Aqueous (hydrogels) or organic (organogels), depending on whether the aqueous component is water or some organic solvent.
Colloidal or coarse grain, depending on the size of the particles.
Rigid, elastic or thixotropic gels, according to their mechanical properties.

The advantages in the use of gels are, among others: they are well tolerated, easily washable and produce freshness.

For the appropriate selection of the type of gel, it is considered that they must meet the following general characteristics:
pH: neutral or weakly acid, the closest thing to the skin's pH,
physical and chemical stability, as well as compatibility with the active ingredients that are incorporated,
rheological properties must provide the preparation with adequate extensibility and adaptability to the surface and skin cavities. For this, it is recommended that they have plastic-thixotropic type flows, characterized by an increase in fluidity during application, followed by a recovery of the initial texture after the drug has been extended, which allows it to be localized and adhered to the treated area.
The possibility of being eliminated from the treated area by simple washing. However, this recommendation should not, in any case, influence the general appearance of the medication, as, for example, with those pathologies that require the rejection of highly occlusive fatty vehicles and which, logically, are not washable.
They should not stain, as far as possible, neither the skin nor the tissues.
They must not present primary irritation or hypersensitization effects.

The criteria for the selection and formulation of a vehicle should be established, based on the type of skin lesion on which it is to be used. The simple appearance or condition of the affected area may be indicative in this regard.

Due to dermatological pathologies can be classified into three general types: acute, chronic and subacute processes or injuries, of intermediate symptomatology to the two previous ones; the vehicles, in turn, are classified in three groups depending on the type of injury for which they should preferably be used.

Possibility of desiccation of wounds, on the one hand, and the characteristics of occlusion, on the other, are the two properties that, in a general way, are more representative of the vehicles used for the formulation of dermatological medicines used for the treatment of severe and chronic processes.

Among the excipients for the preparation of the gels are gel-forming agents, neutralizing agents, wetting agents, or flavoring and coloring agents. These are derived from a variety of natural and artificial substances that give it its texture, viscosity, stability and microstructure.

The gelling agent is selected from the group comprising: Carbomer, Carbopol 940, Carbopol 940P, Neopol 40, glycerin polyacrylates, crosslinked alkyl acrylates, polyacrylamides, acrylic acid polymers, methylcellulose, high molecular weight polyethylene glycol, sodium carboxymethyl cellulose. Those gel-forming agents can be obtained under their trade name, for example: Carbopol, Ultrez 21, Hispogel, Pemlente; Simugel 600, Sepigel 305 and Methocel A.

The neutralizing agents are selected from the group consisting of amines, sodium hydroxide, potassium hydroxide, triethanolamine, aminomethylpropanol, 2,2',2"-nitrilotrietanol.

The wetting agent is selected from the group consisting of polyols, glycerin, sorbitol, propylene glycol, polyethylene glycol, 1,2-propanediol.

The flavoring agent and the colorant are selected from the group comprising natural essences or essential oils; extracts, balsams, compounds isolated from natural essences or from aromatic or artificial sapid chemical compound extracts.

An aqueous solvent is selected from the group comprising purified water and mixtures of watersoluble alcohol-water.

Based on the foregoing, the composition of the present invention, for example, may comprise a gelling agent that is present in an amount equivalent to 0.5 to 1.5% w/w of the composition; a wetting agent that is present in an amount equivalent to 38 to 45% w/w of the composition; a neutralizing agent that is present in an amount equivalent to 0.5 to 1.5% w/w of the composition; a flavoring agent and the colorant which are present in an equivalent amount each not greater than 0.01% w/w of the composition and/or a solvent that is present in a quantity g.s (c.b.p.) 100 grams of the gel.

Thus, it is possible to make a wide range of gel compositions such as those exemplified below:

Example 1. Topical Formulation in Gel

It was prepared a gel composition containing:

| Component | g |
| --- | --- |
| Pirfenidone | 8 |
| M-DDO | 0.016 |
| Carbomer 940 | 1 |
| Propylene glycol | 40 |
| Triethanolamine | 1 |
| Purified water q.s | 100 |

Example 2

It was prepared a second composition containing the following elements:

| Component | Kg |
| --- | --- |
| Pirfenidone | 6 |
| M-DDO | 0.02 |
| acrylamide/copolymer of sodium acryloylmethyl fumarate, isohexadecane polysorbate | 1 |
| 2,2',2''-nitrilotrietanol | 1 |
| 1,2-propanediol | 2.5 |
| Floral fragrance | 0.001 |
| Purified water q.s | 100 |

Example 3

A third composition was prepared containing the following elements:

| Component | g |
| --- | --- |
| Pirfenidone | 8 |
| M-DDO | 0.016 |
| Carbomer 940 | 1.00 |
| Propylene glycol | 50 |
| Triethanolamine | 1.00 |
| Purified water q.s | 100 |
| Macrogolglycerol hydroxystearate 40 | 13 |

Example 4

A fourth example of the compositions object of the present invention is presented, which demonstrates that the modalities thereof are limited only to the preservation of the characteristics of all the components in the gel:

| Component | Kg |
| --- | --- |
| Pirfenidone | 8 |
| M-DDO | 0.016 |
| Carbomer 940 | 1 |
| 2,2',2''-nitrilotrietanol | 1 |
| 1,2-propanediol | 40 |
| Pink stain | 0.01 |
| Purified water q.s | 100 |

Next, a process for preparing the topical formulation in gel form is described.

1. Mixture A
   1.1. Place 45 L of purified water in the Reactor.
   1.2. Gradually add the following material: Carbomer 940 (2 kg).
   1.3. Start stirring constantly at 71-rpm±10% for 3 hours with 30 minutes; 5 minutes before finished the 3 hours and 30 minutes, turn on the homogenizer.
   1.4. Homogenize for 5 minutes at a speed of 3900-rpm±10%.

Identify as Mixture "A"

2. Solution "A"
   2.1.1. Place in the stockpot and heat at (45° C.-50° C.) the propylene glycol (100 kg) move the speed controller to position 30 and stir.
   2.1.2. Gradually add PIRFENIDONE (5-METHYL-1-PHENYL-2-(1H)-PIRIDONE), 16.000 Kg and keeping heating at (45° C.-50° C.) until complete dissolution: Keep stirring with the controller speed at position 50 and heating for 30 minutes.
   2.1.3. Gradually add MACROGOLGLICEROL HIDROXIESTEARATO 40 26.000 Kg maintaining the constant agitation and heating at (45-50° C.) until complete dissolution:

Keep stirring with the speed controller in position 50 and heating for 30 minutes.
   2.1.4. Gradually add maintaining the constant agitation and heating at (45-50° C.) until complete dissolution: MODIFIED-DIALLYL DISULFIDE OXIDE AT 2% 1.6 kg. Keep stirring with the controller speed at position 50 and heating for 30 minutes.

Identify as SOLUTION "A"

2.2. SOLUTION "B"
   2.2.1. Place in a 15-liter capacity stainless steel container: 7.4 L Purified Water and 85% triethanolamine 2 kg.
   2.2.2. Stir until obtain a homogenous solution at a speed of 300-rpm±5%.

Identify as SOLUTION "B"

2.3. FINAL MIXTURE
   2.3.1. Add with constant agitation SOLUTION "A" to the Reactor with MIXTURE "A".
   2.3.2. Add with constant agitation SOLUTION "B".
   2.3.3. Shake constantly at a speed of 71-rpm±10%, for 90 minutes.
   2.3.4. After the mixing time, turn on the homogenizer for 15 minutes at a speed of 3900-rpm±10% and maintain the stirring simultaneously for the same period.

Experimental Design

Gene Behavior of Patients with Diabetic Foot Ulcer Treated for One Month with Pirfenidone+MDDO or Ketanserin.

Clinical trials were conducted as of March 2013 in Hospitals of the Federal District, metropolitan area and Guadalajara, Jalisco following patients scrupulously.

We studied 20 patients with diabetic foot ulcers. 10 were treated with 8% pirfenidone and 0.016% MDDO (Kitoscell Q™) and 10 treated with Ketanserina (Sufrexal™).

Prior to the application of the composition, the damaged area is cleaned, either by washing with neutral soap and abundant water or any other cleaning method normally used. In case the patient has the wound covered with gauze, the gauze is impregnated with an antiseptic solution before removing it and thus prevent the granulation tissue from detaching. In case of necrotic tissue, it is necessary to debride the wound to remove it.

Once the damaged area is cleaned and dried, the gel object of the present invention is applied on the wound or ulcer, starting from the outer edge toward the center. It can be used gauze or bandage to place it on the injury.

The clinical/morphological analyzes shown in table 1 were performed by medical specialists who did not know which patients were treated with a certain medication at the first month of treatment (three times a day with 8% pirfenidone gel+0.016% MDDO after cleaning the affected region, and three times a day with ketanserin).

TABLE 1

Percentage of reduction of the relative ulcer volume (RUV) in patients treated with pirfenidone + MDDO and ketanserin, during a month, measured with the Kundin rule in cm.

| Pa-tient | Age | Treat-ment | Initial RUV[1] cm$^3$ | 1$^{st}$ month RUV cm$^3$ | Initial RUV % | First month RUV % | RRUV[2] % |
|---|---|---|---|---|---|---|---|
| 1 | 67 | PFD[3] | 48.0 | 4.0 | 100 | 8.3 | 91.7 |
| 2 | 53 | PFD | 18.0 | 2.1 | 100 | 11.7 | 88.3 |
| 3 | 49 | PFD | 6.4 | 0.4 | 100 | 6.3 | 93.8 |
| 4 | 47 | PFD | 11.8 | 3.4 | 100 | 28.8 | 71.2 |
| 5 | 63 | PFD | 16.0 | 3.1 | 100 | 19.1 | 80.9 |
| 6 | 67 | KTS[4] | 2.5 | 1.5 | 100 | 61.2 | 38.8 |
| 7 | 56 | KTS | 5.9 | 4.3 | 100 | 73.0 | 27.0 |
| 8 | 53 | KTS | 42.0 | 30.8 | 100 | 73.4 | 26.6 |
| 9 | 57 | KTS | 5.0 | 3.0 | 100 | 60.0 | 40.0 |

[1]Relative ulcer volume.
[2]Percentage of reduction of relative ulcer volume.
[3]8% Pirfenidone + 0.016% MDDO
[4]Ketanserin Results Gene Behavior of Patients with Diabetic Foot Ulcer Treated for One Month with Pirfenidone+MDDO or Ketanserin.

Twenty patients with diabetic foot ulcers were studied. Ten were treated with 8% pirfenidone+0.016% M-DDO (Kitoscell Q™) and 10 treated with Ketanserina (Sufrexal™).

The clinical/morphological analyzes shown in Appendix 1 were performed by medical specialists who did not know which patients were treated with a certain drug at the first month of treatment (three times a day with 8% pirfenidone gel+0.016% MDDO after cleaning the affected region, and three times a day with ketanserin).

The difference in the percentage of reduction of the relative ulcer volume of patients treated with Kitoscell Q is evident when compared to the size and dimensions of the ulcer in patients treated with ketanserin. In other words, the wound in the first heals at a higher speed. The photographs show images of representative patients.

The increase of pro-inflammatory cytokines modifies the normal balance, thus inducing the production of TGF-β1. Due to these conditions, there is a delay in re-epithelization and extracellular matrix production, as shown in FIG. 1.

To demonstrate the induction of collagenic and non-collagenic proteins involved in the process of REGENERATION/REPAIR OF THE WOUND and of the proteins that are necessary in the subsequent process of re-epithelialization, we proceeded to take biopsies of ulcerous tissue from each of the patients to analyze the expression of target genes that code for the production of those proteins.

Thus, 83% of patients treated with pirfenidone+MDDO showed a dramatic and significant increase in COL1α expression in the first month of treatment, while only 43% of patients treated with ketanserin showed a slight increase. It is noteworthy that the relative units of gene expression of each of the mentioned genes was 20 to 200 times higher in patients treated with pirfenidone+MDDO.

Another fundamental protein in the process of extracellular matrix formation is TGFβ1.

During the first month of treatment, 50% of patients treated with pirfenidone+MDDO showed an increase in TGFβ1 gene expression. The increase was found in the same patients who expressed high regulation of COL1α. However, in the protocol arm with Ketanserin patients showed an increase in only 29% of them.

The 40% of patients treated with pirfenidone+MDDO showed a considerable increase in TGFβ3 expression in the first month of treatment. The increase was found in the same patients who expressed high regulation of COL1α and TGFβ1.

TGFβ3 is a protein that plays a key role in the re-epithelization of tissues after having suffered considerable and extensive damage.

Finally, 50% of patients treated with pirfenidone+MDDO showed an increase in the expression of KGF (Keratinocyte growth factor) that promotes cell migration, accelerates the regeneration of wounds in response to damage of the skin or its internal structures. KGF is a paracrine growth factor derived from mesenchymal cells that specifically stimulates the growth of epithelial cells.

At last, all these results demonstrate the PIRFENIDONE MODULATOR ROLL IN THE REGENERATION/REPAIR OF WOUNDS. This effect is enhanced by the antiseptic effect of MDDO, by avoiding infection of the wound; it allows the therapeutic effect of PIRFENIDONE.

Although the present invention has been described with respect to a limited number of embodiments, the specific characteristics of an embodiment should not be attributed to other embodiments of the invention. An individual embodiment is not representative of all aspects of the invention. In some embodiments, the compositions or methods may include numerous compounds or steps not mentioned herein. In other embodiments, the compositions or methods do not include, or are substantially free of, compounds or steps not indicated herein. Variations and modifications exist from the described embodiments.

The invention claimed is:

1. A method of treating chronic skin damage in a subject in need thereof, the method comprising administering to skin of the subject a topical pharmaceutical gel composition comprising modified-diallyl disulfide oxide, 5-methyl-1-phenyl-2(1H)-pyridone, and one or more pharmaceutically acceptable excipients; wherein the chronic skin damage is caused by vascular ulcers, decubitus ulcers, arterial ulcers, or venous ulcers.

2. The method of claim 1, wherein the composition comprises from 0.01 to 0.1% weight/weight of modified-diallyl disulfide oxide, from 5 to 10% weight/weight of 5-methyl-1-phenyl-2(1H)-pyridone, and from 89% to 95% weight/weight of one or more pharmaceutically acceptable excipients.

3. The method of claim 1, wherein the one or more pharmaceutically acceptable excipients are gel-forming agents, neutralizing agents, wetting agents, flavoring agents, stains, and aqueous solvent.

4. The method of claim 3, wherein the gel-forming agent is selected from the group consisting of Carbomer, Carbopol 940, Carbopol 940P, Neopol 40, glycerin polyacrylates, crosslinked alkyl acrylates, polyacrylamides, acrylic acid polymers, methylcellulose, polyethylene glycols of high molecular weight, and sodium carboxymethyl cellulose.

5. The method of claim 3, wherein the neutralizing agent is selected from the group consisting of amines, sodium hydroxide, potassium hydroxide, triethanolamine, aminomethylpropanol, and 2,2',2"-nitrilotrietanol.

6. The method of claim 3, wherein the wetting agent is selected from the group consisting of polyols, glycerin, sorbitol, propylene glycol, polyethylene glycol, and 1,2-propanediol.

7. The method of claim 3, wherein the flavoring agent and the stain are selected from the group comprising natural essences, essential oils, extracts, balsams, compounds isolated from natural essences, compounds isolated from aromatic sapid chemical compound extracts, or compounds isolated from artificial sapid chemical compound extracts.

8. The method of claim 1, wherein the composition comprises an aqueous solvent selected from the group comprising water and mixtures of water-soluble alcohol and water.

9. The method of claim 3, wherein the gel-forming agent is present in an amount equivalent to 0.5 to 1.5% weight/weight of the composition.

10. The method of claim 3, wherein the wetting agent is present in an amount equivalent to 38 to 45% weight/weight of the composition.

11. The method of claim 3, wherein the neutralizing agent is present in an amount equivalent to 0.5 to 1.5% weight/weight of the composition.

12. The method of claim 3, wherein the flavoring agents and the dye stains are each present in an amount not greater than 0.01% weight/weight of the composition.

13. The method of claim 1, wherein the chronic skin damage is caused by vascular ulcers.

14. The method of claim 1, wherein the chronic skin damage is caused by decubitus ulcers.

15. The method of claim 1, wherein the chronic skin damage is caused by arterial ulcers.

16. The method of claim 1, wherein the chronic skin damage is caused by venous ulcers.

17. The method of claim 1, wherein the composition comprises:
   (i) 8% 5-methyl-1-phenyl-2(1H)-pyridone by weight;
   (ii) 0.016% modified-diallyl disulfide oxide by weight;
   (iii) 1% Carbomer 940 by weight;
   (iv) 40% propylene glycol by weight;
   (v) 1% triethanolamine by weight; and
   (vi) 49.984% water by weight.

18. The method of claim 1, wherein the composition comprises:
   (i) 8% 5-methyl-1-phenyl-2(1H)-pyridone by weight;
   (ii) 0.016% modified-diallyl disulfide oxide by weight;
   (iii) 1% Carbomer 940 by weight;
   (iv) 50% propylene glycol by weight;
   (v) 1% triethanolamine by weight;
   (vi) 13% macrogol-glycerol hydroxystearate by weight; and
   (vii) 26.984% water by weight.

19. The method of claim 1, wherein the composition comprises:
   (i) 6% 5-methyl-1-phenyl-2(1H)-pyridone by weight;
   (ii) 0.02% modified-diallyl disulfide oxide by weight;
   (iii) 1% acrylamide/copolymer of sodium acryloylmethyl fumarate, isohexadecane polysorbate by weight;
   (iv) 1% 2,2',2"-nitrilotrietanol by weight;
   (v) 2.5% 1,2-propanediol by weight; and
   (vi) 89.479% water by weight.

20. The method of claim 1, wherein the composition comprises:
   (i) 8% 5-methyl-1-phenyl-2(1H)-pyridone by weight;
   (ii) 0.016% modified-diallyl disulfide oxide by weight;
   (iii) 1% Carbomer 940 by weight;
   (iv) 1% 2,2',2"-nitrilotrietanol by weight;
   (v) 40% 1,2-propanediol by weight; and
   (vi) 49.974% water by weight.

* * * * *

UNITED STATES PATENT AND TRADEMARK OFFICE
CERTIFICATE OF CORRECTION

PATENT NO. : 11,576,905 B2
APPLICATION NO. : 16/638621
DATED : February 14, 2023
INVENTOR(S) : José Agustín Rogelio Magaña Castro et al.

It is certified that error appears in the above-identified patent and that said Letters Patent is hereby corrected as shown below:

In the Claims

In Claim 12, at Column 13, Line 42, the text: "and the dye stains are each present in an amount not greater" should be replaced with the text --and the stains are each present in an amount not greater--.

Signed and Sealed this
Twenty-third Day of May, 2023

Katherine Kelly Vidal
*Director of the United States Patent and Trademark Office*